United States Patent [19]

Kashket

[11] 4,368,272

[45] Jan. 11, 1983

[54] DEVICE FOR IDENTIFYING AND LOCATING DENTAL MICROORGANISMS

[75] Inventor: Shelby Kashket, Chestnut Hill, Mass.

[73] Assignee: Forsyth Dental Infirmary for Children, Boston, Mass.

[21] Appl. No.: 129,682

[22] Filed: Mar. 12, 1980

[51] Int. Cl.³ .................... C12M 1/32; C12Q 1/24; C12M 1/26; A46B 1/00

[52] U.S. Cl. ..................... 435/293; 15/201; 15/210 R; 435/30; 435/287; 435/292; 435/805; 435/810

[58] Field of Search ............ 435/292, 293, 294, 295, 435/299, 287, 317, 803, 805, 810, 34, 36, 29, 30; 15/104 A, 209 R, 210 R, 201 R

[56] References Cited

U.S. PATENT DOCUMENTS

| | | | |
|---|---|---|---|
| 885,276 | 4/1908 | McDonald | 15/209 R |
| 1,668,216 | 5/1928 | Noel | 15/201 |
| 2,904,474 | 9/1959 | Förg | 435/30 X |
| 3,040,352 | 6/1962 | Vian | 15/104 A |
| 3,232,710 | 2/1966 | Rieckmann et al. | 435/14 X |
| 3,718,543 | 2/1973 | Lagomarsino | 435/292 X |
| 3,746,624 | 7/1973 | Hoerman et al. | 435/36 |
| 3,814,670 | 6/1974 | Freake et al. | 435/34 X |
| 3,834,983 | 9/1974 | Conway et al. | 162/146 X |
| 3,881,993 | 5/1975 | Freake et al. | 435/292 X |
| 3,890,200 | 6/1975 | Jordan et al. | 435/800 X |
| 3,902,969 | 9/1975 | Gold | 435/800 X |
| 3,960,652 | 6/1976 | Conway et al. | 162/146 X |

*Primary Examiner*—Robert J. Warden
*Attorney, Agent, or Firm*—Richard P. Crowley

[57] ABSTRACT

A method for identifying and locating dental microorganisms and a device for use in the method, wherein a strip of flexible material, having a back site identifying surface and a front velvet-like surface, is placed in contact with a selected site in the oral cavity, to retain microorganisms on the velvet-like surface, and then the microorganism-containing surface is used to transfer the microorganisms onto suitable substrates that will make possible their identification.

2 Claims, 3 Drawing Figures

DEVICE FOR IDENTIFYING AND LOCATING DENTAL MICROORGANISMS

BACKGROUND OF THE INVENTION

The detection and localization of microorganisms and specific bacterial colonies which are identified with dental caries or oral diseases are a matter of importance. It has been found that *Streptococcus mutans* is identified with dental caries, and selective medium has been discovered for the specific identification of *Streptococcus mutans* from human dental plaque through the use of selective agents which allow the undiminished recovery of the *Streptococcus mutans* with maximum inhibition (see U.S. Pat. No. 3,890,200, issued June 17, 1975). In addition, methods for identification of *Streptococcus mutans* colonies employing other oral streptococci also have been discovered (see, for example, U.S. Pat. No. 3,902,969, issued Sept. 2, 1975).

In the detection and identification of the specific sites of bacterial colonies on the surface of teeth and the soft tissues of the mouth, various techniques of identification have been employed. For example, bacteriological probes have been applied to individual sites on the oral surfaces of the teeth or on the oral surface of the mouth, in order to sample bacterial content, and, thereafter, using normal identification methods to identify the specific bacteria taken from the specific sites. In another technique, impressions of the teeth are made with dental materials. Both techniques have been used in research laboratories; however, both techniques are tedious and are not suitable for routine clinical use by a dentist or for screening a large number of patients, and, therefore, there exists a need for a device to provide for the replication of dental flora on the surfaces of the teeth or the soft tissue of the mouth, to detect and to identify the sites of the microorganisms in a simpler, easier, less complex and less costly manner.

SUMMARY OF THE INVENTION

My invention relates to a dental flora-replica device and to a method of using the device to identify and locate the sites of cariogenic and other microorganisms on the surface of teeth and in the oral cavity.

I have discovered a simple, effective and low-cost dental flora-replica device useful both in identifying microorganisms in the oral cavity and also in locating the position of the microorganisms in the oral cavity.

The dental flora-replica device of the invention comprises a flexible, thin strip of sterile sheet material, typically of plastic or paper, having a back surface and a front surface, the back identifying surface capable of being marked or premarked in a means and manner to identify the position of the designated teeth against which the flexible strip is to be contacted or pressed or that portion of the oral cavity in which the strip is to be used. The front surface is characterized by a soft, velvet-like or plush surface adapted to retain on the surface the microorganisms from the surfaces so contacted, such as from the surfaces of the teeth or from the soft tissue of the oral cavity.

Optionally, the flora-replica device may contain a handle or other means for making it easier for the user to hold onto the strip of material, while introducing the material into the oral cavity and pressing it against the teeth surfaces or soft tissue. In addition and optionally, the flora-replica device may comprise a masking tape or other means over the front surface of the device, in order to protect the device from contamination prior to its use. The device should be thin and flexible, so that it may be pressed into intimate, close contact with the surfaces of the teeth desired or with the soft tissue of the mouth. The front surface thereof should have a sterile, microorganism-free, velvet-like, suede-like or other soft, fuzzy surface, all hereinafter referred to as a velvet-like surface, and which surface is composed of a material adapted to retain, adsorb, absorb or hold otherwise the microorganisms on the surfaces of the teeth or soft tissue, when the soft, velvet-like surface is pressed in contact therewith. The velvet-like surface should be free of contamination and preferably in a sterile condition or sterilized prior to use, so that only the microorganisms of the oral cavity would show up in the detection step.

The identifying back surface may comprise a surface which has been premarked in squares, blocks or other form or preidentified as to the teeth against which the velvet-like surface is to be pressed. Preferably, the back surface is a surface adapted to receive a writing or printing thereon, such as through the marking by the user with a water-insoluble marking pen. The velvet-like front surface may be composed of a variety of natural or synthetic fibrous or particulate material. Typical fibrous materials, for example, which may be employed include, but are not limited to, cotton, polyesters, nylon, rayon, cellulose, or other materials which are not carcinogenic and which are capable of being sterilized. The velvet-like surface may comprise a suede surface, a tufted surface, a flock surface or any soft plush surface characterized by a velvet-like surface which is adapted to fit about and to contact the contours of the teeth and to absorb and retain the microorganisms on the teeth surfaces; that is, capable of being transferred from the teeth surfaces to the velvet-like surface.

The flora-replica device may be used to identify sites that are colonized by one or more specific, for example, cariogenic, bacteria, such as *Streptococcus mutans*, or other microorganisms that cause or are likely to effect oral diseases. In use, my method involves placing a sterile strip of the velvet-like surface against the teeth surfaces or soft tissues and then touching the velvet-like surface one or more times to one or more bacteriological plates or culture media; for example, that contain agar and various selected media, that will permit the specific bacteria transferred from the velvet-like surface to grow, multiply and be identified. Therefore, for example, the particular culture media and the methods of identifying *Streptococcus mutans*, as set forth and used in the prior art, may be employed with the dental flora-replica device.

In the identification of the microorganisms from the velvet-like surface of the strip material, the strip material is pressed into contact on one or a series of different plates, each of the plates being specific as to specific bacteria and with specific tests or onto the surface of other culture media, such as in a petri dish. The particular plates may be premarked in the same manner as the strip material, so that the user may correlate and mark sites on the back of the strip material with the identification of the bacteria cultured on the plates, or the plates may be such that they are marked during use by the dentist or clinician, in accordance with the markings on the particular strip material. In this manner, a single contacting of the teeth surfaces and the use of a single velvet-like surface of strip material may be used to contact the series of plates and to identify one or a plurality of microorganisms on a particular tooth surface and the sites of the microorganisms.

Means are employed with the dental flora-replica device, in order to identify the position of the designated teeth or the soft tissue of the mouth against which the velvet-like surface is pressed in use. In one embodiment, the back surface of the flexible strip of material used as the flora-replica device is marked or is adapted for marking, to identify the position of the designated teeth, and the strip material is so placed on the culture media that the marks are coincident with the position indicators on the plates. The bacteriological plates or culture media are suitably incubated to permit bacterial clones or growth to develop. The clinician, researcher or other person then may identify those teeth and the sites on the particular teeth that are colonized by the specific microorganisms detected in the bacteriological tests; thus permitting for the first time the rapid, simple and low-cost identification of the microorganisms, together with the sites from which the microorganisms are taken.

The dental flora-replica device shall be described for the purpose of illustration only in connection with two embodiments—a simple device for the identification of dental flora from smooth teeth surfaces and another device for the particular use with occlusion tooth-surface evaluation. My dental flora-replica device makes the sampling of large surfaces; for example, one entire quadrant of the oral cavity, simple and rapid, in comparison to prior-art techniques.

The dental flora-replica device will be described for the purpose of illustration only in connection with specific embodiments; however, it is recognized that those persons skilled in the art may make various changes and modifications in the device and method, all without departing from the spirit and scope of the invention.

DESCRIPTION OF THE EMBODIMENTS

Figure 1:
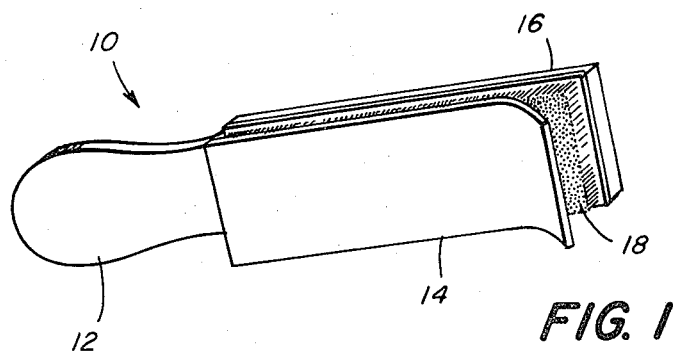
FIG. 1 is a schematic, illustrative view of one embodiment of the dental flora-replica device.

FIG. 1 shows a dental flora-replica device 10 having a short, contoured handle portion 12, so that the sterile device may be handled in use without the contacting of a sterile surface. The device includes a back surface 16 capable of being marked with a pen. The strip device is flexible and thin and has a front surface 18 comprising a sterile velvet-like surface, particularly of a raised plurality of cotton or nylon loop-fiber material. A masking tape 14 on the surface of the velvet material 18 is adapted to be peeled away prior to use and is used to retain the surface 18 in a sterile condition prior to use.

In use, the masking tape 14 is peeled away to expose the sterile velvet-like surface 18, the device 10 is inserted into the oral cavity by holding onto the handle 12, and the strip is then pressed against the hard surfaces of the teeth, with the marking portion marked previously or later, to identify the sites of the teeth against which the device 10 is placed. After removal from the oral cavity, the velvet-like surface, containing the contaminated microorganisms from the contact, is then touched to the surface of a culture medium in a petri dish or to the surface of a bacteriological plate for specific identification of a selected microorganism. After culturing and identifying of the microorganism, the comparison between the marking sites on the back surface 16 and the position on the identifying plate is made to identify the sites of the detected microorganism.

Figure 2:
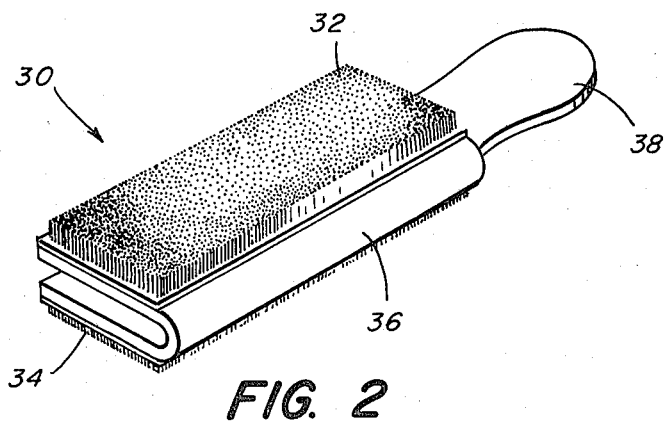
FIG. 2 is a schematic, illustrative view of another embodiment of a dental flora-replica device useful for occlusal surface evaluation.
Figure 3:
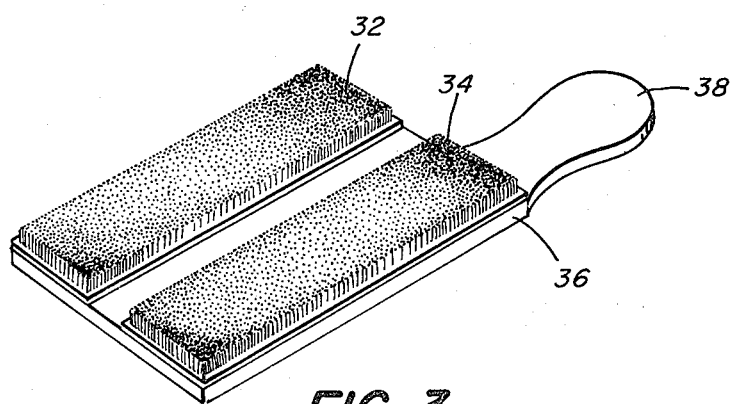
FIG. 3 is an illustrative, representative view of the device of FIG. 2 in an open position for use in the application of the device to a bacteriological detection plate.

FIGS. 2 and 3 are directed to a dental flora-replica device 30 particularly adapted for use with occlusal surfaces and comprises two, elongated, separate, velvet-like surfaces 32 and 34 secured to a plastic backing 36 which is soft and flexible, serving, with the intervening portion between 32 and 34, as a hinge means, so that the surfaces may be placed in opposing, outward positions, as illustrated in FIG. 2. The device contains a handle 38 and a masking tape for the surfaces 32 and 34 (not shown), to maintain the velvet-like surfaces in a sterile condition. The device is shown in FIG. 2 in a position for insertion into the mouth of a patient; for example, between the upper and lower molars. The hinge surface of the occlusal surface replica device 30, like the device 10 surface, is adapted to be marked for identification, so that the particular molars thereof may be identified.

FIG. 3 shows the occlusal surface replica device 30 in a flat, open condition, after contacting or pressing against the occlusion teeth surfaces, and ready to be applied or for the application of one or more bacteriological-detection plates to the surfaces 32 and 34. Thereafter, the comparison between the contacted plates and the replica device 30 will identify the particular sites of the microorganisms so identified.

If desired, the bacteriological-detection means used may be marked on a portion thereof identical to the portion on the back surface of the flora-replica device, so that direct comparison between the device and the plates or petri dish is not required after identification of the microorganisms.

What I claim is:

1. A dental flora-replica device particularly for use in occlusal teeth surfaces, which device is used for identifying and locating the sites of cariogenic or other microorganisms on the occlusal surfaces of teeth, which device comprises:
   (a) a flexible, thin strip of sheet material having a front and a back surface;
   (b) the front surface comprising first and second, separate, spaced-apart, elongated, generally parallel strips of sterile, velvet-like surfaces composed of a material to retain microorganisms, when the occlusal surfaces of opposing teeth are pressed against each of the velvet-like surfaces;
   (c) hinge means so that the first and second surfaces may be placed in an opposing relationship and in contact with occlusal teeth of a patient;
   (d) the back surface marked to locate the site of the designated occlusal teeth whose microorganisms are to be identified and located; and
   (e) a removable masking-tape means secured over the first and second velvet-like surfaces, to protect the sterile first and second surfaces prior to use, whereby in use the occlusal, dental replica device may be folded, with the first and second velvet-like surfaces extending outwardly from the top and bottom to contact the occlusal teeth, and, thereafter, the device placed in an open, flat position for application to a bacteriological identification means to identify the microorganisms retained on the first and second velvet-like surfaces.

2. The device of claim 1 which includes a handle means secured at one end of the device, to permit introduction of the device into the oral cavity.

* * * * *